United States Patent [19]

Bimbi

[11] Patent Number: 5,480,491
[45] Date of Patent: Jan. 2, 1996

[54] PROCESS FOR THE PREPARATION OF CRYSTALLINE LACTULOSE FROM COMMERCIAL SYRUPS

[75] Inventor: Giuseppe Bimbi, Pontedera, Italy

[73] Assignee: Inalco S.p.A., Milan, Italy

[21] Appl. No.: 229,559

[22] Filed: Apr. 18, 1994

[30] Foreign Application Priority Data

Apr. 28, 1993 [IT] Italy ................... MI93A0833

[51] Int. Cl.$^6$ ................. C13F 1/00; C13F 1/02; C13T 1/06; C13D 3/12
[52] U.S. Cl. .............. 127/61; 127/46.2; 127/55; 127/56; 127/58
[58] Field of Search ................. 127/61, 58, 56, 127/55, 46.2

[56] References Cited

U.S. PATENT DOCUMENTS

| | | | |
|---|---|---|---|
| 4,555,271 | 11/1985 | Carobbi et al. | 127/46.2 |
| 4,978,397 | 12/1990 | Carobbi et al. | 127/46.2 |
| 5,034,064 | 7/1991 | Deya et al. | 127/46.2 |
| 5,304,251 | 4/1994 | Tomita et al. | 127/42 |

FOREIGN PATENT DOCUMENTS

| | | | |
|---|---|---|---|
| 0132509 | 2/1985 | European Pat. Off. | C13K 13/00 |
| 0159521 | 10/1985 | European Pat. Off. | C08F 8/42 |
| 0158148 | 6/1988 | European Pat. Off. | C13K 13/00 |
| 0284959 | 1/1992 | European Pat. Off. | C08F 8/42 |
| 0284960 | 6/1992 | European Pat. Off. | C08F 8/42 |

OTHER PUBLICATIONS

J. Agric. Chem. 1984, 32, 288–292 Jul./Dec. 1983.

Primary Examiner—Paul Lieberman
Assistant Examiner—Patricia Hailey
Attorney, Agent, or Firm—Hedman, Gibson & Costigan

[57] ABSTRACT

The following description sets forth a new process for the preparation of ≧98.5% pure crystalline lactulose from commercially available aqueous syrups having the following composition: 50–70% by weight of lactulose, 3–9% by weight of lactose, 3–14% by weight of galactose, 4–7% by weight of other carbohydrates, the total content of carbohydrates different from lactulose being of from 10% to 30%.

8 Claims, No Drawings

PROCESS FOR THE PREPARATION OF CRYSTALLINE LACTULOSE FROM COMMERCIAL SYRUPS

FIELD OF THE INVENTION

The present invention relates to a process for the preparation of high-purity crystalline lactulose by crystallization of commercially available aqueous syrups.

PRIOR ART

Lactulose, or 4-0-β-D-galactopyranosyl-D-fructofuranose, is a semisynthetic disaccharide, used in the form of syrup or of crystalline product on account of its laxative action, efficacy in the treatment of hepatic dysfunctions, in particular of portal systemic encephalopathy, and as a sweetener.

Lactulose syrups that are now available on the market are generally not pure, but contain more or less large amounts of other carbohydrates, in particular galactose and lactose, and typically 50% by weight of lactulose; from 5 to 8% by weight of galactose; from 3 to 5% by weight of lactose; from 5 to 10% by weight of other carbohydrates.

As may be seen, the per cent amount of carbohydrates different from lactulose contained in the syrups of commerce is relatively high. The use of products containing other carbohydrates in addition to lactulose for the therapy of disorders requiring administration of lactulose alone, would be prejudicial and raise problems, e.g. in patients suffering from diabetes or requiring a diet without galactose.

Therefore, as lactulose becomes ever more important in pharmaceutical practice, there is a need for an adequate purification of same from contaminating carbohydrates.

As disclosed in U.S. Pat. No. 4,536,221, various processes known for lactulose purification are based on the crystallization from alcoholic solvents, usually ethanol.

However, the lactulose crystals obtained from alcohols always contain a given amount of solvent, probably due to the formation of hydrogen bonds between the OH groups of sugar and the OH groups of the solvent, while the solvent residue cannot be completely removed even by prolonged dryings.

The disadvantage of the crystallization from ethanol is not only that complex process are required for solvent residue elimination, but also that high operating costs are generally involved.

Some process for the direct recovery of lactulose from aqueous solutions based on the concentration of same by drying under vacuum, lyophilization, and spray-drying are also known.

Some of them are mentioned below:
the process disclosed in JP No. 61,104,800, which comprises concentrating an aqueous solution containing at least 60% lactulose, adding the concentrate with crystal seeds at from 60° to 110° C., kneading and pulverizing, thus affording a powder containing lactulose crystals;
the process disclosed in European patent application EP-A-333,295, for the preparation of solid lactulose from an aqueous syrup by high-temperature evaporation to lower the water content to 10% max., followed by cooling, grinding, sieving or crumbling of the resulting solid, whose purity is the same as that of the starting syrup;
the process disclosed in European patent application EP-A-480,519, consisting of lactulose solidification from aqueous solutions by evaporating the water contained therein and conversion of the resulting product into a free-flowing powder. Lactulose solidification may be initiated by addition of crystal seeds, preferably in amounts of from 1% to 5% by weight (on dry residue basis);
the process disclosed in patent application JP No. 2,200,693, ("Derwent" abstract) consisting of lactulose crystallization from a condensed syrup, followed by condensate drying at a reduced pressure and pulverization of the dried product.

The aforementioned processes are essentially based on the evaporation and concentration of the starting syrup and greatly differ from crystallizations in that they simply cause the solute solidification without eliminating—as crystallizations do—the undesirable secondary components present in mother liquors.

Therefore, since the processes based on concentration give lactulose of the same purity as that of the starting syrup, they cannot be utilized for the production of high-purity lactulose from commercial syrups that, as already mentioned, contain high amounts of other carbohydrates. Furthermore, the aforementioned processes can give crystalline lactulose only if combined with crystallization from alcohols.

The only known process which involves a real crystallization from water, with no need of alcoholic solvents, is disclosed in EP-A- 318,630 by the Applicant. It is also the only known process that yields highly pure (≧98%) and non-hygroscopic crystalline lactulose. However, this process cannot be exploited if the lactulose aqueous syrup to be crystallized contains carbohydrates different from lactulose in amounts exceeding 14% by weight of lactulose.

In case of lactulose syrups containing carbohydrates different from lactulose in amounts exceeding said limit value, it was always deemed it necessary to lower the content of said carbohydrates below said limit value and, to this purpose, before crystallization from water, the aqueous syrup was always purified according to one of the other known methods.

The ever growing importance of lactulose in pharmaceutical practice is a spur to the development of new processes to be applied to the industrial production of high-purity crystalline lactulose, without causing the inconveniences of the processes already known.

SUMMARY

The Applicant has now found a new process for lactulose purification that may be exploited on an industrial scale, yielding high-purity crystalline lactulose, in particular having a content of carbohydrates different from lactulose lower than 1% and a purity higher than 98.5%. The present process is based on the crystallization of a commercial lactulose aqueous syrup having a total content of carbohydrates different from lactulose higher than 10% by weight.

In particular, the process of the present invention can be applied to commercial lactulose aqueous syrups having the following composition: from 50% to 70% by weight of lactulose; from 3% to 9% by weight of lactose; from 3% to 14% by weight of galactose; from 4% to 7% by weight of other carbohydrates; the total content of carbohydrate different from lactulose ranging between 10% and 30% by weight.

It has surprisingly been found—and this finding constitutes a fundamental feature of the present invention—that by adding a commercial lactulose aqueous syrup with trihydrated crystalline lactulose in amounts ranging from 5% to 30% of the total lactulose present, a high-purity lactulose crystallizes in good yields.

As known, in crystallization processes, once the right solvent and the right crystallization conditions in respect of concentration and temperature have been found, few seed crystals are generally enough for initiating the progressive crystallization of the product in solution, according to laws governed by:

product concentration in the concentrated matrix;
crystallization temperature;
residence time.

As far as sugars are concerned, said conditions are generally reached in such long times that a "random self-initiation" of the solutes having lower $k_{ps}$ than the product to be crystallized becomes highly probable: consequently, the crystallized cake recovered is still contaminated by said solutes.

It is, therefore, surprising that the addition to a lactulose aqueous syrup of a large amount of trihydrated lactulose in the crystal state—and not of few seed crystals—can initiate a preferential crystallization of lactulose in respect of the other carbohydrates present in the syrup, yielding a high-purity crystalline lactulose.

Compared with the process disclosed in European patent application EP-A-318630, the process of the present invention has the advantage of giving very-high-purity crystalline lactulose starting from any syrup of commerce.

DETAILED DESCRIPTION OF THE INVENTION

Lactulose crystallization according to the present invention is characterized by the following process: the water content of the lactulose aqueous syrup is lowered to a sugar concentration of from 70° to 80° Brix; the resulting syrup is added at from 5° C. to 20° C. with crystalline trihydrated lactulose, acting as a crystallization initiator, in amounts ranging from 5% to 30% by weight of the lactulose present in the starting syrup, which temperature is maintained for a period of from 20 to 120 hrs. The crystalline solid obtained consisted of trihydrated lactulose having a content of carbohydrates different from lactulose below 1% by weight and a lactulose content of at least 98.5% (on anhydrous basis).

In particular, the process for the preparation of crystalline lactulose according to the present invention comprises the following steps:
a) commercial lactulose aqueous syrup is evaporated under continuous stirring at a temperature of from 50° to 60° C. and at a pressure of 2660 to 6650 Pa, up to a sugar concentration of 70°–80° Brix;
b) the resulting concentrated syrup is cooled to 5° to 20° C. and added with crystalline trihydrated lactulose in an amount of from 5 to 30 parts by weight of the lactulose present in the syrup;
c) the suspension obtained is stirred at said temperature for a period of from 20 to 120 hours and the lactulose present in the syrup is crystallizes in the form of trihydrated lactulose;
d) the crystallized trihydrated lactulose obtained is separated by centrifuging or filtering from mother liquors, washed with cold water, and dried at a pressure of from 6650 to 13300 Pa, at a temperature of from 30° to 60° C., to yield crystalline lactulose having a water content below 0.5%.

The process of the invention gives highly pure (98.5% minimum) crystalline lactulose in yields per cycle greater than 40% of the lactulose present in the starting syrup.

The mother liquors resulting from the separation of crystalline trihydrated lactulose are passed once or several times through columns containing anionic or cationic exchange resins, either individually or in sequence, as illustrated in European patent applications EP-A-132,509, EP-A-158,148, EP-A-159,521, EP-A-284,959, and EP-A-294,960 by the Applicant, so to lower the content of carbohydrates different from lactulose below the aforesaid limits and, therefore, to allow the mixing of same with the commercial starting syrup to be subjected to the process of the present invention.

This operation allows the recycling of the mother liquors and the almost complete recovery of the lactulose present in the syrups of commerce.

In a preferred embodiment of the present invention, the concentrated syrup of step b) has a content of 55% to 62% by weight of lactulose and the crystalline trihydrated lactulose is added in an amount ranging between 5% and 15% by weight of the lactulose present in the commercial syrup (the amount of trihydrated lactulose used as a crystallization initiator is expressed as % by weight of anhydrous lactulose).

A single washing of the crystalline trihydrated lactulose obtained in d) with cold water (3°–5° C.) is generally enough for a satisfactory removal of the residual mother liquors and fop obtaining a product of the desired purity.

The following examples illustrate some embodiments of the claimed process.

EXAMPLES

Crystallization of Lactulose Starting From Commercially Available Syrups

Several crystallizations of commercially available lactulose syrups were carried out according to the standard procedure described below.

Syrups characteristics are shown in Table 1 and the results obtained in Table 2.

STANDARD PROCEDURE

A syrup (1000 kg) of composition as shown in Table 1 was concentrated under vacuum at a pressure of from 2660 to 6650 Pa, under continuous stirring, at a temperature of from 50° to 60° C., to a sugar concentration of 70°–80° Brix.

The resulting solution was fed to a crystallizer and cooled to 8° C. under continuous stirring. Once said conditions have been reached, crystalline trihydrated lactulose was fed in the amounts shown in Table 2.

The obtained suspension was slowly stirred at 8° C. for the period indicated in Table 2, then the mother liquors were removed by centrifuging, the crystal cake was squeezed to remove most mother liquors, washed with cold water, and squeezed again.

The resulting product was dried in an air oven at a temperature not exceeding 60° C. and at a pressure of from 6650 to 13300 Pa, until obtaining anhydrous lactulose crystals (i.e. having a maximum water content of 0.5%) of >98.8% purity (on dry basis) (Table 2).

The purity of lactulose crystals was determined on the dried product by HPLC analysis (J. Agric. Food Chem., 32, 288–292, 1984), by means of comparison with standard lactulose produced and sold by MERCK.

TABLE 1

| Composition (%) of the aqueous solutions used | | | | | | |
|---|---|---|---|---|---|---|
| Item | LTL | LTS | EPI | GLT | ND | H$_2$O |
| I | 51.4 | 4.4 | 1.2 | 3.6 | 6.4 | 34.0 |
| II | 50.6 | 4.9 | 2.0 | 3.8 | 5.0 | 33.7 |
| III | 51.9 | 3.1 | 2.2 | 7.9 | 3.1 | 31.8 |
| IV | 51.0 | 8.2 | 1.3 | 3.5 | 4.0 | 32.0 |

Remarks: all quantities are by weight percentages of the solution total weight.

Abbreviations
LTL lactulose;
LTS lactose;
EPI epilactose;
GLT galactose;
ND carbohydrates different from LTL, LTS, EPI, and GLT.

TABLE 2

Experimental results

| Ex. | Syr.$^a$ | °Brix$^b$ | h$^c$ | LTL %w$^d$ | Conc. syr. Kg$^e$ | LTL as initiator %$^f$ | LTL as initiator Kg$^g$ | total LTL kg$^h$ | LTL recovered Kg$^i$ | LTL recovered % tit$^l$ | LTL recovered % tit$^m$ | yield$^n$ |
|---|---|---|---|---|---|---|---|---|---|---|---|---|
| 1 | I | 74 | 72 | 55.2 | 931 | 18.7 | 111.6 | 610 | 309 | 84.2 | 99.0 | 42.2 |
| 2 | I | 74 | 96 | 55.3 | 929 | 7.5 | 46.1 | 553 | 254 | 83.8 | 98.9 | 38.5 |
| 3 | I | 74 | 72 | 55.3 | 929 | 10.0 | 61.1 | 565 | 260 | 84.6 | 99,2 | 38.9 |
| 4 | II | 78 | 120 | 57.0 | 888 | 5.0 | 30.3 | 531 | 212 | 83.9 | 99.0 | 33,5 |
| 5 | II | 74 | 72 | 55.0 | 920 | 7.5 | 45.2 | 544 | 253 | 84.1 | 99.4 | 38.9 |
| 6 | III | 75 | 88 | 55.6 | 933 | 7.5 | 46.5 | 558 | 310 | 83,4 | 99,0 | 46.3 |
| 7 | III | 71 | 88 | 54.4 | 954 | 7.5 | 46.7 | 558 | 255 | 84.0 | 98,8 | 38.4 |
| 8 | IV | 74 | 56 | 55.2 | 924 | 15.0 | 69.8 | 587 | 238 | 83,5 | 99,1 | 33.9 |
| 9 | IV | 74 | 72 | 55.5 | 919 | 7.5 | 45.8 | 548 | 248 | 84,6 | 98,8 | 38,3 |
| 10 | IV | 70 | 72 | 53.8 | 948 | 7.5 | 45.9 | 548 | 213 | 84,6 | 98,8 | 32.9 |

$^a$Commercial aqueous syrup used
$^b$Brix degrees after syrup concentration
$^c$Residence time in crystallizer at 8° C.
$^d$By weight %, amount of LTL after syrup concentration
$^e$Amount of concentrated syrup (kg)
$^f$By weight % amount of trihydrated LTL used as a crystallization initiator
$^g$Weight of trihydrated LTL used as a crystallization initiator
$^h$LTL total weight (LTL of the syrup + LTL used as a crystallization initiator)
$^i$Weight of trihydrated LTL recovered
$^l$titre of anhydrous LTL in trihydrated crystal before drying
$^m$titre of anhydrous LTL after drying
$^n$yield calculated by:

(anhydrous) crystalline LTL recovered (kg)
  (anhydrous) total LTL in the system (kg)

I claim:

1. A process for the preparation of crystalline lactulose having a content of carbohydrates which are different from lactulose that is lower than 1% and a lactulose content of more than 98.5%, said process comprising the following steps:

(a) evaporating a part of the water from an aqueous lactulose syrup under continuous stirring at a temperature of from 50° to 60° C. and at a pressure of from 2660 to 6650 Pa to obtain a concentrated lactulose syrup with a sugar concentration of 70°–80° Brix, said aqueous lactulose syrup having a lactulose content of from 50% to about 62% by weight and a content of carbohydrates which are different from lactulose and include lactose, galactose and other carbohydrates, the lactose content being from 3% to 9% by weight; the galactose content being from 3% to 14 % and the other carbohydrate content being from 4% to 7% by weight;

(b) cooling the concentrated syrup obtained in step (a) to a temperature of from 5° to 20° C. prior to adding from 5% to 30% by weight of crystalline trihydrated lactulose based on the total weight of lactulose which is present in said aqueous lactulose syrup;

(c) stirring the product of step (c) for a period of from 20 to 120 hours to crystallize the lactulose which is present as trihydrated lactulose;

(d) separating the crystallized trihydrated lactulose by centrifugation or filtration of the product of step (c) to obtain a mother liquor and separated crystallized trihydrated lactulose; and thereafter washing said separated crystallized trihydrate of lactulose with cold water prior to drying the separated crystallized trihydrate of lactulose at a temperature of from 30° to 60° C., to obtain crystalline lactulose having a water content of less that 0.5%.

2. The process according to claim 1, wherein the crystalline trihydrated lactulose is added in an amount of between 5% and 15% by weight of the lactulose present in said aqueous lactulose syrup.

3. The process according to claim 1, wherein the mother liquors obtained in step (d) are passed one or more times through columns containing ion exchange resins to reduce the content of carbohydrates which are other than lactulose.

4. The process according to claim 3, wherein the mother liquors which are recovered after the passage through the ion exchange columns are mixed with the aqueous lactulose syrup of step (a).

5. A process for the preparation of crystalline lactulose having a content of carbohydrates which are different from lactulose that is lower than 1% and a lactulose content of more than 98.5%, said process consisting essentially of the following steps:

(a) evaporating a part of the water from an aqueous lactulose syrup under continuous stirring at a temperature of from 50° to 60° C. and at a pressure of from 2660 to 6650 Pa to obtain a concentrated lactulose syrup with a sugar concentration of 70°–80° Brix, said aqueous lactulose syrup having a lactulose content of from 50% to about 62% by weight and a content of carbohydrates which are different from lactulose and include lactose, galactose and other carbohydrates, the lactose content being from 3% to 9% by weight; the galactose content being from 3% to 14 % and the other carbohydrate content being from 4% to 7% by weight;

(b) cooling the concentrated syrup obtained in step (a) to a temperature of from 5° to 20° C. prior to adding from 5% to 30% by weight of crystalline trihydrated lactulose based on the total weight of lactulose which is present in said aqueous lactulose syrup;

(c) stirring the product of step (c) for a period of from 20 to 120 hours to crystallize the lactulose which is present as trihydrated lactulose;

(d) separating the crystallized trihydrated lactulose by centrifugation or filtration of the product of step (c) to obtain a mother liquor and separated crystallized trihydrated lactulose; and thereafter washing said separated crystallized trihydrate of lactulose with cold water prior to drying the separated crystallized trihydrate of lactulose at a temperature of from 30° to 60° C., to obtain crystalline lactulose having a water content of less that 0.5%.

6. The process according to claim 5, wherein the crystalline trihydrated lactulose is added in an amount of between 5% and 15% by weight of the lactulose present in said aqueous lactulose syrup.

7. The process according to claim 5, wherein the mother liquors obtained in step (d) are passed one or more times through columns containing ion exchange resins to reduce the content of carbohydrates which are other than lactulose.

8. The process according to claim 7, wherein the mother liquors which are recovered after the passage through the ion exchange columns are mixed with the aqueous lactulose syrup of step (a).

* * * * *